United States Patent [19]

Denzel et al.

[11] Patent Number: 5,194,604
[45] Date of Patent: Mar. 16, 1993

[54] PROCESS AND INTERMEDIATES FOR BETA-LACTAMS HAVING AMINOTHIAZOLE(IMINOOXYACETIC ACID)ACETIC ACID SIDECHAINS

[75] Inventors: Theodor Denzel, Regensburg, Fed. Rep. of Germany; Christopher M. Cimarusti, Millstone, N.J.; Janak Singh, Lawrenceville, N.J.; Richard H. Mueller, Ringoes, N.J.

[73] Assignee: E. R. Squibb & Sons, Inc., Princeton, N.J.

[21] Appl. No.: 546,622

[22] Filed: Jun. 29, 1990

[51] Int. Cl.$^5$ ................ C07D 417/14; C07D 501/38
[52] U.S. Cl. .................... 540/222; 540/221; 540/225; 540/228; 540/316; 540/363; 540/364
[58] Field of Search .......... 540/222, 221, 215, 225, 540/316, 363, 364, 355

[56] References Cited

U.S. PATENT DOCUMENTS

| | | | |
|---|---|---|---|
| 3,704,294 | 11/1972 | Kishida et al. | 260/239.1 |
| 4,258,041 | 3/1981 | O'Callaghan et al. | 424/246 |
| 4,386,034 | 5/1983 | Floyd et al. | 260/456 |
| 4,409,214 | 10/1983 | Takaya et al. | 424/246 |
| 4,500,526 | 2/1985 | Imae et al. | 514/226 |
| 4,533,660 | 8/1985 | Gordon et al. | 514/210 |
| 4,600,772 | 7/1986 | O'Callaghan et al. | 544/625 |
| 4,775,670 | 10/1988 | Sykes et al. | 514/210 |
| 4,782,147 | 12/1988 | Ochiai et al. | 540/335 |
| 4,904,775 | 2/1990 | Sundeen et al. | 540/363 |

FOREIGN PATENT DOCUMENTS

| | | |
|---|---|---|
| 93376A2 | 11/1983 | European Pat. Off. |
| 0097961 | 1/1984 | European Pat. Off. |
| 0267733 | 5/1988 | European Pat. Off. |
| 0342423 | 11/1989 | European Pat. Off. |
| 60-112789 | 6/1985 | Japan |

OTHER PUBLICATIONS

Chemical Abstracts, vol. 105, No. 17, Oct. 27, 1986, p. 667, column 2, abstract No. 152 768f.

Chemical Abstracts, vol. 104, No. 11, Mar. 17, 1986, p. 640, column 1, abstract No. 88 359y.

*Primary Examiner*—Nicholas S. Rizzo
*Attorney, Agent, or Firm*—Timothy J. Gaul

[57] ABSTRACT

Disclosed herein are processes for preparing a compound of the formula

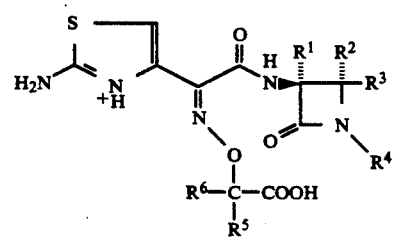

in which a novel compound of the formula

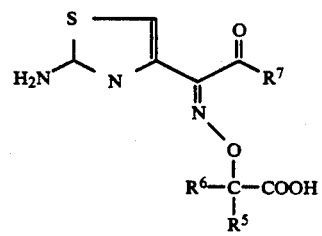

is reacted with a beta lactam of the formula

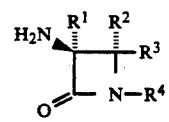

by treatment with a base, wherein the symbols are as defined in the specification.

37 Claims, No Drawings

PROCESS AND INTERMEDIATES FOR BETA-LACTAMS HAVING AMINOTHIAZOLE(IMINOOXYACETIC ACID)ACETIC ACID SIDECHAINS

FIELD OF THE INVENTION

This invention relates to preparation of beta-lactams having aminothiazole(iminooxyacetic acid)acetic acid sidechains and novel intermediates thereof. Such compounds are useful, inter alia, as antibacterial agents or as intermediates in the preparation thereof.

BACKGROUND OF THE INVENTION

The $\beta$-lactam ring

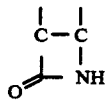

has been known since the late nineteenth century. Since then, myriad penicillins, cephalosporins, and monobactams have been discovered (see the discussion of prior art in U.S. Pat. Nos. 4,775,670 and 4,533,670, issued Oct. 4, 1988 and Aug. 6, 1985, respectively). One recently discovered antibiotic is aztreonam ("Azactam"®), which has the structure

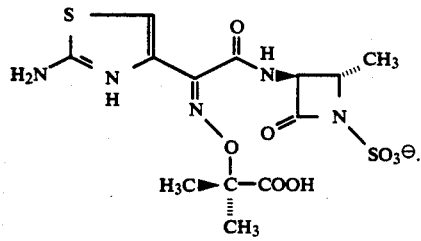

(see U.S. Pat. No. 4,775,670). Another recently discovered antibiotic is tigemonam, which has the structure

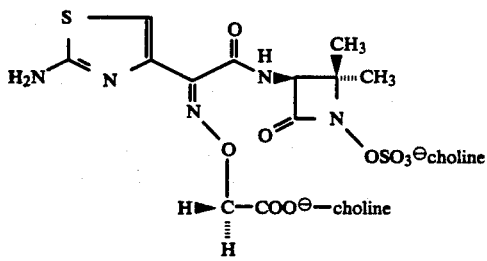

(see U.S Pat. No. 4,533,660).

Still other beta-lactam antibiotics are ceftazidime, which has the structure

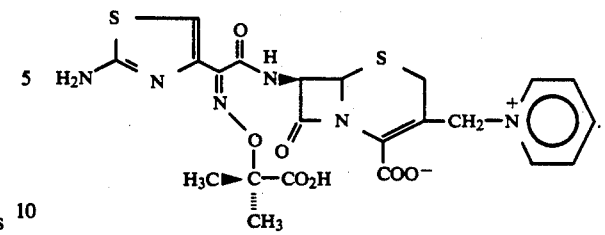

(see inter alia U.S. Pat. Nos. 4,258,041 and 4,600,772); cefixime, which has the structure

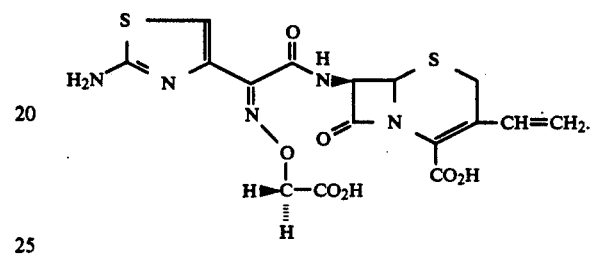

(see inter alia U.S. Pat. No. 4,409,214); and carumonam sodium, which has the structure

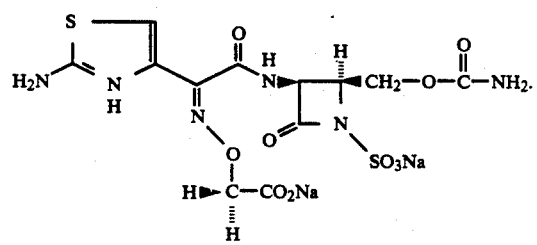

(see inter alia European patent application no. 93,376 A2).

Such antibacterial agents possess aminothiazolyl-(iminooxyacetic acid)acetic acid sidechains. Many such compounds are described in the literature; see, for example, United Kingdom patent application no. 2,071,650 (published Sep. 23, 1981). The art would benefit, therefore, from processes that would efficiently produce beta-lactams having aminothiazolyl(iminooxyacetic acid)acetic acid sidechains.

BRIEF DESCRIPTION OF THE INVENTION

In accordance with the present invention, a process is provided for preparing a compound of the formula

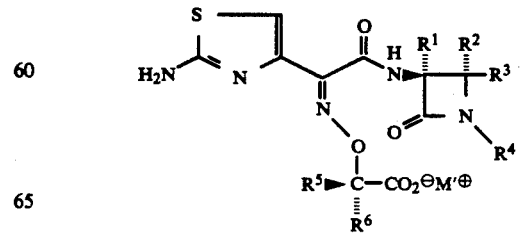

in which a compound of the formula

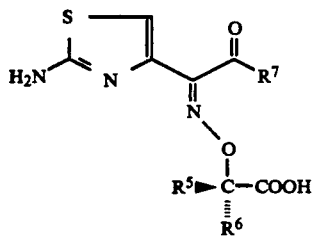

or an acid or amine salt thereof is reacted with a beta lactam of the formula

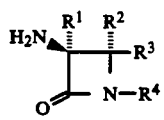

in the presence of a base, after which the product I is recovered therefrom employing conventional isolation procedures.

In compounds I, II, and III and throughout the specification, the symbols above are defined as follows:

$R^1$ is hydrogen or alkoxy of 1 to 4 carbons;
$R^2$ is hydrogen or alkyl;
$R^3$ is hydrogen, alkyl or

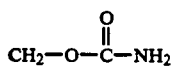

and $R^4$ is hydrogen

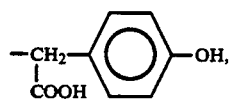

—$SO_3^\ominus M^\oplus$, or —$OSO_3^\ominus M^\oplus$ or $R^3$ and $R^4$ together are

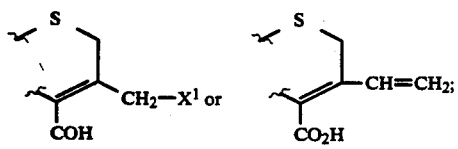

$R^5$ and $R^6$ are the same or different and each is hydrogen or alkyl or $R^5$ and $R^6$ together with the carbon atom to which they are attached are cycloalkyl;

$R^7$ is

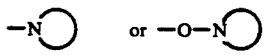

wherein

7-membered heterocyclic ring having at least one nitrogen atom in the ring or such a group fused to a phenyl or substituted phenyl ring;

$M'^\oplus$ and $M^\oplus$ are either or both hydrogen or a cation; and $X^1$ is —OH, —OAc, —Br, —Cl or

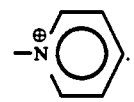

Also in accordance with the present invention, a process is provided for preparing compound I wherein $R^7$ is

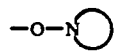

in which a diacid of the formula

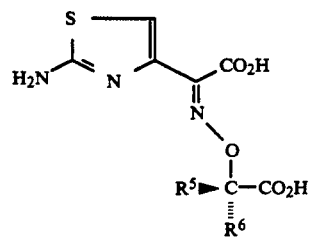

IV is reacted with an alkylhalosilane to form a protected compound of the formula

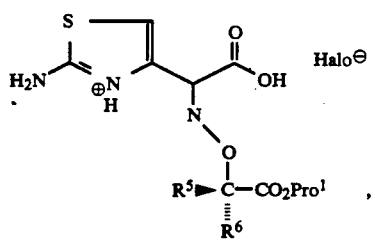

V wherein $Pro^1$ is alkylsilyl, which is reacted in situ with a hydroxy compound of the formula

VI and a coupling reagent (e.g., a carbodiimide such as dicyclohexylcarbodiimide), followed by deprotection with a lower alcohol to form compound II. Compound II may be isolated as an acid salt (e.g., hydrogen halide, sulfonic acid) or an amine salt (e.g., triethylammonium).

Compound II is then reacted with compound III as described above to form compound I.

Further in accordance with the present invention, a process is provided for preparing compound I wherein $R^7$

in which a compound of the formula

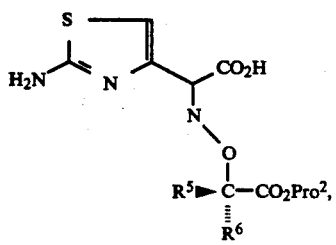

wherein $Pro^2$ is a protecting group (e.g., benzhydryl or t-butyl), is reacted with a compound of the formula

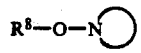

wherein $R^8$ is alkylsulfonyl by treatment with a base to form a protected ester of the formula

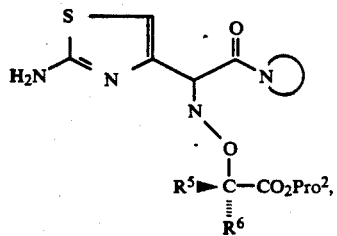

which is deprotected by treatment with a strong acid such as trifluoroacetic acid, optionally in the presence of a reagent such as anisole, to form compound II. Compound II, which may be isolated as described previously, is then reacted with compound III as described above to form compound I.

Also in accordance with the present invention, compound II is a novel and integral part of the invention and is generally useful in the preparation of beta-lactam antibiotics possessing aminothiazole(iminooxyacetic acid)acetic acid sidechains, as described herein. In compound II, it is preferred that $R^5$ and $R^6$ are methyl or hydrogen and that $R^7$ is

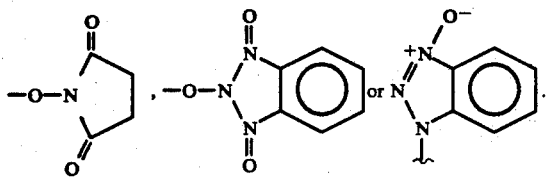

For compound II and the processes of this invention, it is also preferred that $R^1$, $R^2$, etc. correspond to substituents in the desired products aztreonam, tigemonam, ceftazidime, cefixime, and carumonam sodium. This methodology is, however, applicable to preparation of many other antibiotics possessing an aminothiazole(iminooxyacetic acid) acetic acid sidechain.

DETAILED DESCRIPTION OF THE INVENTION

Listed below are definitions of various terms used to describe this invention. These definitions apply to the terms as they are used throughout the specification (unless they are otherwise limited in specific instances) either individually or a part of a larger group.

The terms "alkyl" and "alkoxy" refer to both straight and branched chain hydrocarbon groups having 1 to 10 carbon atoms. The term "lower alkyl" refers to groups having 1 to 4 carbon atoms.

The term "cycloalkyl" refers to cyclic hydrocarbon groups having 3, 4, 5, 6, or 7 carbon atoms in the ring.

The term "cation", as used throughout the specification, refers to any positively charged atom or group of atoms. The "—$SO_3^{\ominus}M^{\oplus}$" and "—$OSO_3^{\ominus}M^{\oplus}$" substituents on the nitrogen atom of the β-lactams of this invention encompass all sulfonic acid salts. Pharmaceutically acceptable salts are preferred for $M^{\oplus}$ and $M'^{\ominus}$, although other salts are also useful in purifying the products of this invention or as intermediates for the preparation of pharmaceutically acceptable salts. The cationic portion of the salts of this invention can be obtained from either organic or inorganic bases. Such cationic portion includes, but is not limited to, the following ions: ammonium; substituted ammonium, such as alkylammonium (e.g., tetra-n-butylammonium, referred to hereinafter as tetrabutylammonium); alkali metal, such as lithium, sodium and potassium; alkaline earth metal, such as calcium and magnesium; pyridinium; dicyclohexylammonium; hydrabaminium; benzathinium; choline; and N-methyl-D-glucaminium.

The term "lower alcohol" refers to alkyl groups of 1 to 4 carbon atoms linked to a hydroxyl group. Exemplary lower alcohol groups are methanol, ethanol, propanol, isopropyl alcohol, and butanol.

The term "substituted phenyl" refers to a phenyl group substituted with 1, 2, or 3 amino, halogen, hydroxy, trifluoromethyl, alkyl (of 1 to 4 carbon atoms), or alkoxy (of 1 to 4 carbon atoms) groups.

The expression "a 4, 5, 6, or 7-membered heterocyclic ring" refers to substituted and unsubstituted, aromatic and non-aromatic cyclic rings having one or more (preferably 1, 2 or 3) nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl. One type of "4, 5, 6 or 7-membered heterocycle" is the "heteroaryl" group. The term "heteroaryl" refers to those 4, 5, 6 or 7-membered heterocycles which are aromatic. Exemplary heteroaryl groups are substituted and unsubstituted pyridinyl, 1,2,3-triazolyl, 1,2,4-triazolyl, imidazolyl, thiazolyl, thiadiazolyl, triazinyl, and tetrazolyl. Preferred groups are

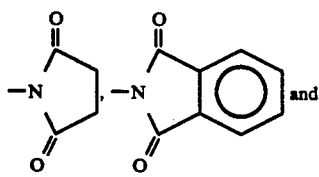

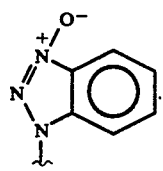

The starting compound of the formula

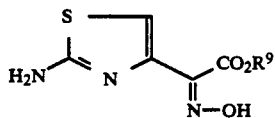   X is known. In compound X and throughout the specification, $R^9$ is alkyl of 1 to 4 carbon atoms.

Compound X is reacted with an alkylating agent such as bromoisobutyric acid, $R^{10}$ ester (ethyl preferred), bromoacetic acid, $R^{10}$ ester (ethyl preferred) or other substituted bromoacetic acid esters at about 25° to 100° C. (about 80° to 90° C. preferred) in the presence of an alkali or alkaline earth metal base (e.g., potassium carbonate or sodium carbonate) in an organic solvent (e.g., dimethylformamide) to form

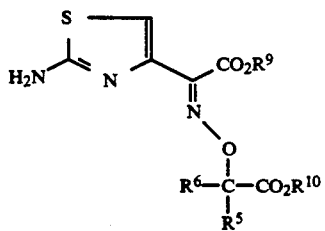   XI wherein $R^{10}$ is lower alkyl, phenyl(lower alkyl), diphenyl(lower alkyl) or substituted phenyl(lower alkyl).

Compound XI is saponified in water or an alcohol solvent with an aqueous base (e.g., sodium or potassium hydroxide) at about 25° to 80° C. (45° to 55° C. preferred) to form compound IV. Compound IV, in turn, is reacted with an alkylhalosilane (trimethylchlorosilane preferred) at about 25° to 80° C. (about 45° to 55° C. preferred) in an organic solvent (dimethylformamide preferred) to form compound V. The protecting group in compound V ($Pro^1$) is trialkylsilyl or phenyldialkylsilyl (trimethylsilyl preferred).

Compound V is reacted with the hydroxy compound VI by treatment with a coupling reagent such as diisopropylcarbodiimide or dicyclohexylcarbodiimide (which is preferred) at about −20° to 25° C. (about −10° to 0° C. preferred) in an organic solvent (e.g., ethyl acetate, dichloromethane, dimethylformamide) and then deprotected by treatment with a lower alcohol (methanol preferred) in an organic solvent (e.g., ethyl acetate, dichloromethane, dimethylformamide) at about −20° to 25° C. (about 0° to 10° C. preferred) to form compound II wherein $R^7$ is

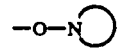

When $R^7$ comprises an oxygen atom as above,

is preferred to be

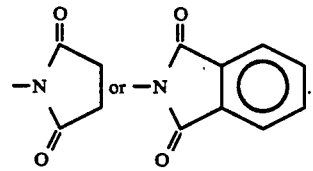

Alternatively, compound II may be derived from the known compound VII. In compound VII, $Pro^2$ is a protecting group such as diphenylmethyl (which is preferred) or t-butyl. For this route, compound VI is reacted with an alkylsulfonyl halide (methanesulfonyl chloride preferred) at about 10° to 30° C. in an organic solvent (e.g., acetonitrile) in the presence of a base (triethylamine preferred) to provide compound VIII. Compound VII is then reacted with compound VIII in which

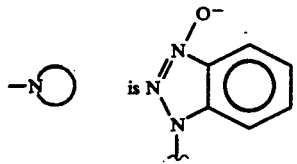

in an organic solvent (e.g., acetonitrile) in the presence of a base such as triethylamine (which is preferred), tributylamine and diisopropyl ethyl amine under an inert atmosphere (e.g., argon) at about 10° to 40° C. (about 20° to 30° C. preferred) to form compound IX.

Compound IX, in turn, is deprotected by treatment with a strong acid such as trifluoroacetic acid or methanesulfonic acid (which is preferred) under an inert atmosphere (e.g., argon) in an organic solvent (e.g., methylene chloride) at about −30° to 20° C. (about −20° to 0° C. preferred) to form compound II wherein $R^7$ is and preferably is

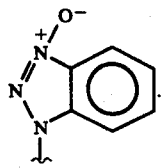

Compound II and compound III (which may be generated in situ as described in Example 2) are optimally reacted at about −10° to 20° C. in the presence of a base for control of pH at about 8.0 to 8.5 to form compound I. Exemplary bases for use in this reaction are triethylamine, sodium hydroxide, potassium hydroxide, sodium carbonate, potassium carbonate, sodium bicarbonate, potassium bicarbonate, and the like. The preferred base is triethylamine. A salt of compound II is preferred, such as an amine salt with methanesulfonic acid or an acid salt with triethylamine.

When $R^4$ is $-SO_3^-M^+$, compound III is preferred to be prepared by reacting a compound of the formula

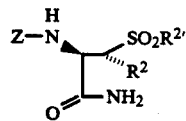
XII (wherein Z is benzyloxycarbonyl and $R^{2'}$ is alkyl, aryl, aralkyl or alkylaryl) first with a halosulfonic acid-pyridine complex (2,6-lutidinechlorosulfonic acid preferred) in an organic solvent. The so-reacted compound XII is next reacted, preferably in situ, with a base selected from alkali metal hydroxides, carbonates, and bicarbonates (sodium hydroxide preferred) in aqueous solution to form compound III wherein one of $R^2$ and $R^3$ is hydrogen and $R^4$ is $-OSO_3^-M^+$. Further reaction conditions are shown in Example 2. See also U.S. Pat. No. 4,386,034.

The invention will now be further described by the following working examples. These examples are preferred embodiments of the invention for the preparation of aztreonam and are meant to be illustrative rather than limiting. All temperatures are in degrees Celsius. As a shorthand reference, the compound prepared in part A of an example will be referred to as "compound A", and likewise for compounds prepared in parts B, C, D, etc.

EXAMPLE 1

2[[[1-(2-Amino-4-thiazolyl)-2-[(2-methyl-4-oxo-1-sulfo-3-azetidinyl)amino]-2-oxoethylidene]amino]oxy]-2-methylpropanoic acid

A. 1-[(Methylsulfonyl)oxy]-1H-benzotriazole

Hydroxybenzotriazole (5.4 g) was suspended in acetonitrile (50 ml) and cooled to 16° C. under argon. Triethylamine (6.1 ml) was added to give a hazy, colorless solution. A solution of methanesulfonyl chloride (4.7 g) in acetonitrile (5 ml) was added dropwise over 3 minutes to keep the temperature below 30° C. The resulting solution was stirred for 1 hour in a 16° C. bath, diluted with ethyl acetate (150 ml), and filtered to remove the solid triethylamine hydrochloric acid. The solid was then rinsed with ethyl acetate (100 ml). The colorless filtrate was washed with 1:1 water: saturated sodium chloride (100 ml), 1:1:1 water: saturated sodium chloride:sodium bicarbonate (75 ml), 1:1 water:saturated sodium chloride (2×50 ml), and sodium chloride (50 ml), and dried over magnesium sulfate. The solution was filtered and the filtrate concentrated in vacuo to give white crystalline compound A (8.27 g, 97%). A 99% yield was obtained by Itoh et al., Bull. Chem. Soc. Japan 51 (11), 3320–3329 (1978).

Melting point: 90°–92.5° C.

B.
(Z)-2-[[[1-(2-Amino-4-thiazolyl)-2-oxo-2-(3-oxo-1H-benzotriazol-1-yl)ethylidene]-amino]oxy]-2-methylpropanoic acid, diphenylmethyl ester and

C.
(Z)-2-Amino-α-[[2-(diphenylmethoxy)-1,1-dimethyl-2-oxoethoxy]imino]-4-thiazoleacetic acid, 1H-benzotriazol-1-yl ester A suspension of 2-aminothiazolyl-4-α-(benzhydryloxycarbonyl-dimethyl-methoxyimino)acetic acid (7.04 g) in acetonitrile (80 ml) was prepared at room temperature under argon. Triethylamine (2.40 ml) was added to give a hazy colorless solution. Compound A (3.41 g) was added to give a hazy yellow solution, which was stirred for 4 hours at room temperature. Thin layer chromatography (TLC) showed formation of a 74:26 mixture of compound B:compound C.

D.
(Z)-2-[[[1-(2-Amino-4-thiazolyl)-2-(3-oxido-1H-benzotriazol-1-yl)-2-oxoethylidene-]amino]oxy]-2-methylpropanoic acid, diphenylmethyl ester, methanesulfonate (1:1) salt The B:C mixture was filtered, and the filtrate was diluted with 40 ml of ethyl acetate and cooled to −12° C. under argon. Methanesulfonic acid (1.0 ml) was added dropwise over 1 to 2 minutes to the filtrate solution, which was then stirred for 15 minutes. The suspension was diluted with ethyl acetate (150 ml), stirred for 5 minutes, filtered under nitrogen, rinsed with ethyl acetate (120 ml), and dried in vacuo at room temperature to give compound D as a fine white solid (7.1 g, 68% yield from compound A).

E.
(Z)-2-[[[1-(2-Amino-4-thiazolyl)-2-(3-oxido-1H-benzotriazol-1-yl)-2-oxoethylidene]amino]oxy]-2-methylpropanoic acid, methanesulfonate (1:1) salt Compound D (6.52 g) was suspended in methylene chloride (60 ml). Anisole (2.0 ml) was added, and the suspension was cooled to −14° C. under argon. Methanesulfonic acid (3.3 ml) was added dropwise over 1 to 2 minutes, and the solution was stirred for 2.5 hours at −14° to −6° C. (about 0.5 hour at −14° C., 1 hour at −10° C., and 1 hour at −6° C). The solution was diluted with methylene chloride (50 ml) and slowly ethyl acetate (300 ml) was added at a rate to keep the reaction temperature below 0° C. (A −10° C. bath may be used to help control the exothermic reaction.) The mixture was stirred for 1.5 hours at −2° C. (although 0.5 hour may be sufficient), filtered under nitrogen, washed with ethyl acetate (75 ml), and dried in vacuo to give compound E as a fine white solid (4.457 g, 91.6% yield).

F. [2S-2α,3β(Z)]]-3-[[(2-Amino-4-thiazolyl)[(1-carboxy-1-methylethoxy)imino]acetyl]amino]-2-methyl-4-oxo-1-azetidinesulfonic acid Compound D from Example 2 (0.901 g) was suspended in 30% aqueous ethanol (9.8 ml) and cooled to −6° C. Triethylamine (3.0 ml) was added to give a clear, colorless solution. Compound E (2.44 g) was added portionwise over 1 hour, and the solution was rinsed with aqueous ethanol (0.7 ml). This solution was stirred for an additional 2 hours at 31 6° to −3° C. Concentrated hydrochloric acid (1.75 ml) was added dropwise, and within 2 minutes the product compound F started to precipitate. The mixture was let stand for 2.5 hours at −3° to 0° C., filtered, the solid rinsed with 1:1 water:95% ethanol (2×2 ml) and ethanol (2×2 ml), and dried for 16 hours at room temperature in vacuo to give compound F (2.38 g, 81 molar percent yield, uncorrected) solvated with aqueous ethanol.

EXAMPLE 2

2S-[2α,3β(Z)]]-3-[[(2-Amino-4-thiazolyl)[(1-carboxy-1-methylethoxy)imino]acetyl]amino]-2-methyl-4-oxo-1-azetidinesulfonic acid

A. (Z)-2-Amino-α-[(2-ethoxy-1,1-dimethyl-2-oxo-ethoxy)imino]-4-thiazoleacetic acid, ethyl ester 2-(2-Amino-4-thiazolyl)-2-hydroxyimino ethanoic acid, ethyl ester (100 g) was dissolved in 300 ml of dimethylformamide at room temperature in a three-necked round bottom flask fitted with a mechanically driven paddle stirrer, thermometer, and condenser. Bromoisobutyric acid, ethyl ester (100 g) and ground potassium carbonate (64 g) were added, and the mixture was heated to 85° C. for 4 to 5 hours until thin layer chromatography (TLC) indicated the reaction was complete. The reaction mixture was then cooled to 40° C., slowly added to 1000 ml of ice-water, and stirred for 1 hour at 15 to 20° C. The resulting precipitate solidified and was collected with suction. The filter cake was washed with water (4×300 ml) until the filtrate showed neutral pH and dried (tray or fluid bed drier) at 30° C. to obtain compound A (147 g).

B. (Z)-2-Amino-α-[(1-carboxy-1-methylethoxy)-imino]-4-thiazoleacetic acid

Potassium hydroxide pellets (40 g, 85% content) were dissolved in 500 ml water in a three-necked, round bottom flask fitted with a mechanically driven paddle stirrer, pH electrode, and thermometer (temperature may rise to 50° C.). Compound A (100 g) was added, and the suspension was maintained at 50° C. After 1 to 2 hours, the precipitate disappeared and the pH decreased to 11. A clear solution indicated a complete reaction, which was confirmed by TLC. The temperature was adjusted to 20° C. and the pH to 2.0 with concentrated hydrochloric acid (about 60 ml). Compound B precipitated. The precipitate was stirred for 1 hour at 20° C., collected with suction, washed with water (4×250 ml), and dried at 40° C. (tray or fluid bed) to a final water content of 7 to 10%. The resulting crude product was suspended in isopropanol (400 ml), heated to reflux for 3 hours, cooled to 20° C., collected with suction, washed with isopropanol (3×50 ml), dried at 40° C. in vacuo to obtain 71 g of compound B, with a final water content of less than 0.3%.

C. (Z)-2-Amino-α-[(1-carboxy-1-methylethoxy)imino]-4-thiazoleacetic acid, 2,5-dioxo-1-pyrrolidinyl ester, methanesulfonate salt Compound B (109.2 g) was added to dimethylformamide (500 ml) in a 1-liter flask. 300 ml of the dimethylformamide were distilled off on a rotary evaporator. Trimethylchlorosilane (70 ml) was added at 50° C. and agitated for 15 minutes. Excess trimethylchlorosilane was removed in vacuo, and the remaining solution was added to a 1-liter, three-necked flask equipped with a thermometer, magnetic stirring bar and dropping funnel. The solution was then cooled to −5° C. in an ice-/sodium chloride bath. With agitation, 50 g of N-hydroxysuccinimide was added, and agitation was continued for 3 minutes.

Dicyclohexylcarbodiimide (95 g) dissolved in ethyl acetate (450 ml) was added with agitation via a dropping funnel at such a rate (45 to 60 minutes) that the temperature did not exceed 5° C. (external cooling was required). Agitation was continued at 0° C. for 2 more hours and TLC indicated completeness of the reaction. Triethylamine (30 g) was added at 0° C. via a dropping funnel over 1 minute, the precipitate filtered, the cake washed with 4:1 ethyl acetate/dimethylformamide (200 ml) and ethyl acetate (100 ml), and the mother liquor cooled to 5° C. Methanol (20 ml) was added, followed by methanesulfonic acid (36 ml) within 5 minutes, with agitation for 10 minutes at ≦10° C. Ethyl acetate (300 ml) was added with agitation at 5° C. for 20 minutes. The mixture was then filtered, washed with ethyl acetate (200 ml) and dried in vacuo at 25° C. to yield 185.0 g (78.3%) of compound C. Another run, using 54.6 g of compound B, yielded 95.0 g (80.5%) of compound C.

D. (2S-trans)-2-methyl-4-oxo-3-[[(phenylmethoxy)carbonyl]amino]-1-azetidinesulfonic acid, monosodium salt 2,6-lutidine (8.4 ml) was dissolved in methylene chloride (252 ml) and cooled to −20° C. Chlorosulfonic acid (22.4 ml) was slowly added over about 70 minutes, maintaining the temperature below −10° C. After holding the solution at −10° C. for 30 minutes, N-[(phenylmethoxy)carbonyl]-L-threoninamide, methanesulfonate ester (30.0 g) was added with stirring at −10° C. until the reaction was complete, as determined by HPLC and TLC (8:2 ethyl acetate-methanol, Merck silica gel).

The reaction mixture was then added to 200 ml of ice water with the temperature kept below 5° C., and a yellow-brown emulsion formed. The pH was adjusted to about 8.3 with sodium hydroxide (about 190 to 200 ml) with cooling to limit to about a 4° C. increase. The phases were separated and the aqueous phase was reextracted with methylene chloride (112 ml). The aqueous phase was then heated to and held at 35° to 40° C. and pH 8.0 (9.5 ml of 5 N sodium hydroxide) until the reaction was complete (HPLC, TLC as described above). The dissolved methylene chloride was then stripped off at 40° C. under reduced pressure (about 400 mbar) for about 30 minutes. Within two hours thereafter, the solution was cooled to 5° C. and stirred for 30 minutes. The resulting precipitate was collected by suction, washed with ice water (2×20 ml), and dried to yield 27.25 g of compound D.

E.
[(2S-trans)-3-Amino-2-methyl-4-oxo-1-azetidinesulfonic acid, inner salt 150.0 g of the sodium salt from part D were suspended in 1400 ml of methanol/water (1:1) in a 2-liter, three-necked round bottom flask, equipped with a mechanical stirrer, gas inlet tube, and pH electrode. The flask was flushed with nitrogen, palladium on carbon (30.0 g) was added, and a strong hydrogen stream was passed through the mixture. TLC showed completeness of reaction at pH 7.0. The solution was filtered by suction over Diacel ® and the cake was washed with 100 ml of methanol/water (1:1).

F.
[2S-[2α,3β(Z)]]-3-[[(2-Amino-4-thiazolyl)-[(1-carboxy-1-methylethoxy)imino]acetyl]amino]-2-methyl-4-oxo-1-azetidinesulfonic acid The filtrate from part E was transferred to a 4-liter beaker equipped with a mechanical stirrer, pH electrode, thermometer, and dropping funnel. The temperature was adjusted to 0° C. and the pH to 8.0 with triethylamine. Compound C (225.5 g) was added portionwise and the pH was maintained at 8.0 to 8.5 with triethylamine. After TLC verified completeness, the pH was adjusted to 4.3 with concentrated hydrochloric acid. Diacel ® (10 g) was added and agitated for 10 minutes. The Diacel was removed by filtration and the filter cake was washed with 100 ml of methanol/water (1:1). The filtrate was acidified with concentrated hydrochloric acid as rapidly as possible to pH 1.3 at ≦10° C. The solution was then seeded and stirring was stopped for 10 minutes. The solution was then cooled to 0° C. and stirred for 30 minutes. The precipitate was collected by filtration and the filter cake washed with cold methanol/water (2×100 ml). The product was vacuum-dried until a water content of about 12% was reached.

Yield: 174.2 g (90.0%).

What is claimed is:

1. A process for preparing a product of the formula

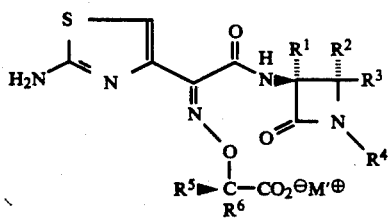

which comprises:
(a) reacting a substrate of the formula

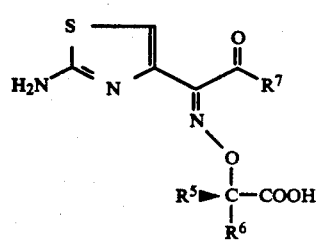

or an acid or amine salt thereof with a beta-lactam of the formula

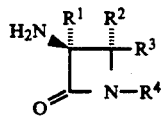

or a salt or inner salt thereof by treatment with a base; and
(b) recovering the product therefrom; wherein:
$R^1$ is hydrogen or alkoxy of 1 to 4 carbons;
$R^2$ is hydrogen or alkyl;
$R^3$ is hydrogen, alkyl, or

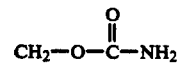

and $R^4$ is hydrogen,

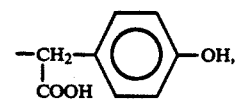

$-SO_3^{\ominus}M^{\oplus}$, $-OSO_3^{\ominus}M^{\oplus}$ or $R^3$ and $R^4$ together are

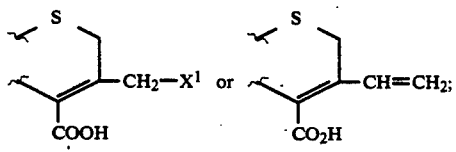

$R^5$ and $R^6$ are the same or different and each is hydrogen or alkyl or $R^5$ and $R^6$ together with the carbon atom to which they are attached are cycloalkyl;
$R^7$ is

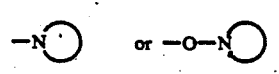

wherein

is a 4, 5, 6 or 7-membered heterocyclic ring having at least one nitrogen atom in the ring or such a group fused to a phenyl or substituted phenyl ring;
$M'^{\oplus}$ and $M^{\oplus}$ are either or both hydrogen or a cation; and
$X^1$ is —OH, —OAc, —Br, —Cl or

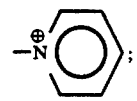

and wherein:
"substituted phenyl" refers to a phenyl group substituted with 1, 2, or 3 amino, halogen, hydroxy, trifluoromethyl, alkyl (of 1 to 4 carbon atoms), or alkoxy (of 1 to 4 carbon atoms) groups.

2. A process for preparing a product of the formula

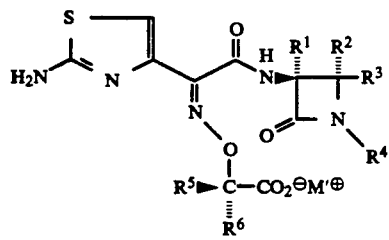

which comprises
(a) reacting a diacid of the formula

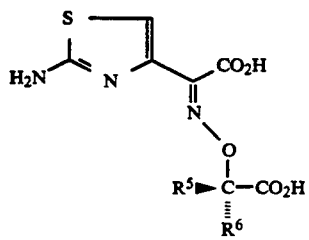

with an alkylhalosilane to form a protected compound of the formula

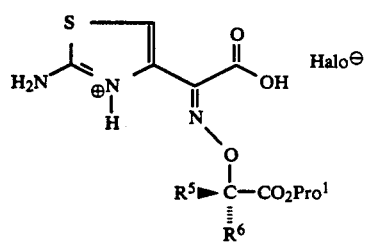

(b) reacting the protected compound with a coupling reagent and a hydroxy compound of the formula

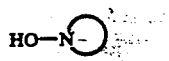

(c) deprotecting the protected compound with a lower alcohol to form a monoacid of the formula

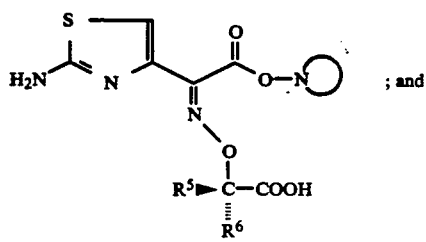

(d) reacting the monoacid or an acid or amine salt thereof with a beta-lactam of the formula

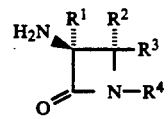

or a salt or inner salt thereof by treatment with a base to form the product;
wherein:
$R^1$ is hydrogen or alkoxy of 1 to 4 carbons;
$R^2$ is hydrogen or alkyl;
$R^3$ is hydrogen, alkyl or

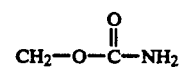

and $R^4$ is hydrogen,

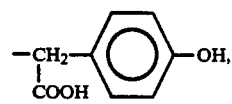

—$SO_3^\ominus M^\oplus$, or —$OSO_3^\ominus M^\oplus$ or $R^3$ and $R^4$ together are

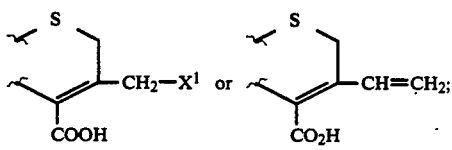

$R^5$ and $R^6$ are the same or different and each is hydrogen or alkyl or $R^5$ and $R^6$ together with the carbon atom to which they are attached are cycloalkyl;

is a 4, 5, 6 or 7-membered heterocyclic ring having at least one nitrogen atom in the ring or such a group fused to a phenyl or substituted phenyl ring;
$Pro^1$ is alkylsilyl;
$M'^\oplus$ and $M^\oplus$ are either or both hydrogen or a cation; and
$X^1$ is —OH, —OAc, —Br, —Cl or

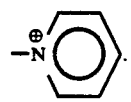

3. The process of claim 2, wherein the diacid is prepared by a process comprising:
saponifying a diester of the formula

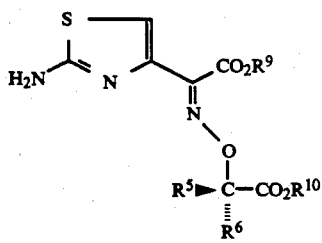

by treatment with an aqueous base in water or an alcohol solvent, wherein $R^9$ is lower alkyl and $R^{10}$ is lower alkyl, phenyl (lower alkyl) diphenyl(lower alkyl) or substituted phenyl (lower alkyl).

4. A process for preparing a product of the formula

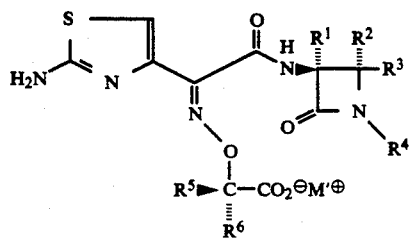

which comprises:

(a) reacting; a first compound of the formula

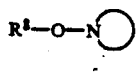

with a second compound of the formula

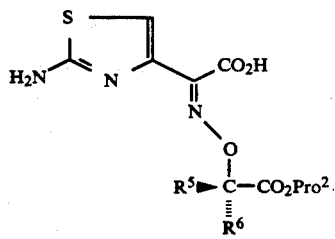

by treatment with a base to form a protected ester of the formula

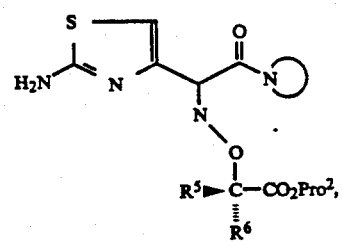

(b) deprotecting the protected ester by treatment with an alkylsulfonic acid to form an acid of the formula

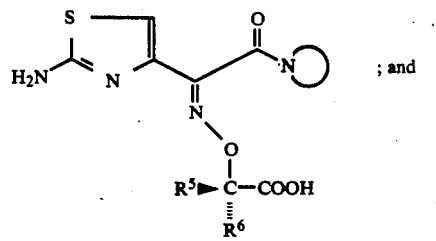

(c) reacting the acid or an acid or amine salt thereof with a beta-lactam of the formula

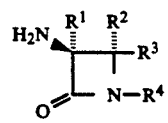

or a salt or inner salt thereof by treatment with a base to form the product;

wherein:

$R^1$ is hydrogen or alkoxy of 1 to 4 carbons;

$R^2$ is hydrogen or alkyl;

$R^3$ is hydrogen, alkyl, or

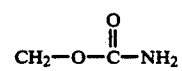

and $R^4$ is

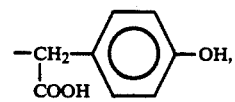

$-SO_3^{\ominus}M^{\oplus}$, or $-OSO_3^{\ominus}M^{\oplus}$ or $R^3$ and $R^4$ together are

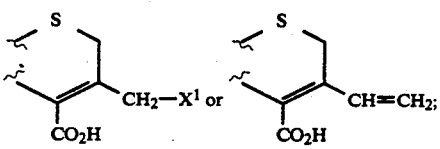

is a 4, 5, 6 or 7-membered heterocyclic ring having at least one nitrogen atom in the ring or such a group fused to a phenyl or substituted phenyl ring;

$R^8$ is alkylsulfonyl;

$Pro^2$ is a protecting group;

$M'^{\oplus}$ and $M^{\oplus}$ are either or both hydrogen or a cation; and $X^1$ is $-OH$, $-OAc$, $-Br$, $Cl$ or

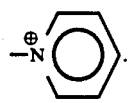

5. The process of claim 1, wherein:
$R^1$ is hydrogen;
one of $R^2$ and $R^3$ is hydrogen and the other is methyl;
$R^4$ is $-SO_3^{\ominus}M^{\oplus}$;
$R^5$ and $R^6$ are methyl; and
$M^{\oplus}$ is hydrogen or a cation.

6. The process of claim 2, wherein:
$R^1$ is hydrogen;
one of $R^2$ and $R^3$ is hydrogen and the other is methyl;
$R^4$ is $-SO_3^{\ominus}M^{\oplus}$;
$R^5$ and $R^6$ are methyl; and
$M^{\oplus}$ is hydrogen or a cation.

7. The process of claim 4, wherein:
$R^1$ is hydrogen;
one of $R^2$ and $R^3$ is hydrogen and the other is methyl;
$R^4$ is $-SO_3^{\ominus}M^{\oplus}$;
$R^5$ and $R^6$ are methyl; and
$M^{\oplus}$ is hydrogen or a cation.

8. The process of claim 1, wherein:
$R^1$, $R^5$ and $R^6$ are hydrogen;
$R^2$ and $R^3$ are methyl;
$R^4$ is $-OSO_3^{\ominus}M^{\oplus}$; and
$M^{\oplus}$ is hydrogen or a cation.

9. The process of claim 2, wherein:
$R^1$, $R^5$ and $R^6$ are hydrogen;
$R^2$ and $R^3$ are methyl;
$R^4$ is $-OSO_3^{\ominus}M^{\oplus}$; and
$M^{\oplus}$ is hydrogen or a cation.

10. The process of claim 4, wherein:
$R^1$, $R^5$ and $R^6$ are hydrogen;
$R^2$ and $R^3$ are methyl;
$R^4$ is $-OSO_3^{\ominus}M^{61}$; and
$M^{\oplus}$ is hydrogen or a cation.

11. The process of claim 1, wherein:
$R^1$ and $R^2$ are hydrogen;
$R^3$ and $R^4$ together are

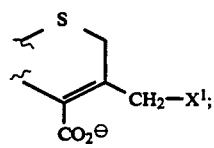

$R^5$ and $R^6$ are methyl; and
$X^1$ is $-OH$, $-OAcetyl$, $-Br$, $-Cl$, or

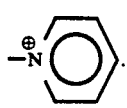

12. The process of claim 2, wherein:
$R^1$ and $R^2$ are hydrogen;
$R^3$ and $R^4$ together are

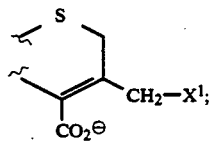

$R^5$ and $R^6$ are methyl; and
$X^1$ is $-OH$, $-OAc$, $-Br$, $-Cl$, or

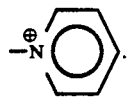

13. The process of claim 4, wherein:
$R^1$ and $R^2$ are hydrogen;
$R^3$ and $R^4$ together are

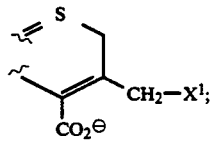

$R^5$ and $R^6$ are methyl; and
$X^1$ is $-OH$, $-OAc$, $-Br$, $-Cl$, or

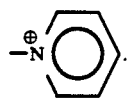

14. The process of claim 1, wherein:
$R^1$, $R^2$, $R^5$, and $R^6$ are hydrogen; and
$R^3$ and $R^4$ together are

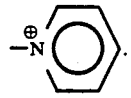

15. The process of claim 2, wherein:
$R^1$, $R^2$, $R^5$, and $R^6$ are hydrogen; and
$R^3$ and $R^4$ together are

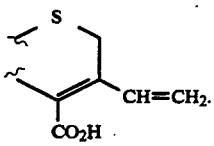

16. The process of claim 4, wherein:
$R^1$, $R^2$, $R^5$, and $R^6$ are hydrogen; and
$R^3$ and $R^4$ together are

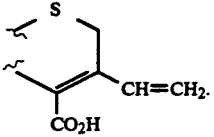

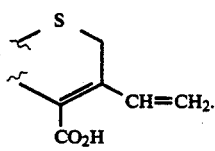

17. The process of claim 1, wherein:
R¹ and R² are hydrogen;
R³ is

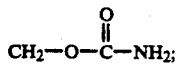

R⁴ is —SO₃⊖M⊕;
R⁵ and R⁶ are hydrogen; and
M⊕ is hydrogen or sodium.

18. The process of claim 2, wherein:
R¹ and R² are hydrogen;

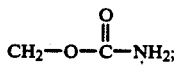

R³ is

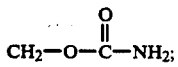

R⁴ is —SO₃⊖M⊕;
R⁵ and R⁶ are hydrogen; and
M⊕ is hydrogen or sodium.

19. The process of claim 4, wherein:
R¹ and R² are hydrogen;
R³ is

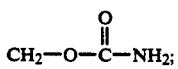

R⁴ is —SO₃⊖M⊕;
R⁵ and R⁶ are hydrogen; and
M⊕ is hydrogen or sodium.

20. The process of claim 1, wherein R⁷ is

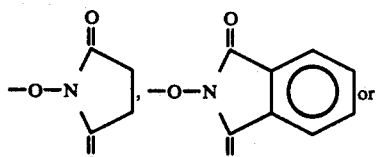

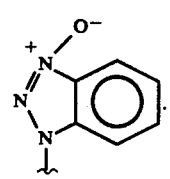

21. The process of claim 2, wherein

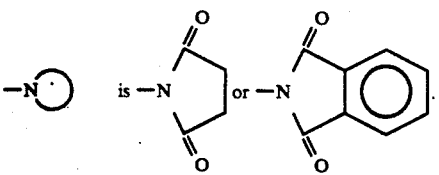

22. The process of claim 4, wherein

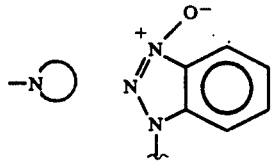

23. The process of claim 1, wherein the base used to treat the substrate is triethylamine.
24. The process of claim 2, wherein the base used to treat the monoacid is triethylamine.
25. The process of claim 4, wherein the base used to treat the acid is triethylamine.
26. The process of claim 2, wherein the alkylhalosilane is trimethylchlorosilane.
27. The process of claim 4, wherein the alkylsulfonic acid is methanesulfonic acid.
28. The process of claim 4, wherein R⁸ is methylsulfonyl.
29. The process of claim 1, wherein the beta lactam is reacted with a methanesulfonic acid-amine salt of the substrate.
30. The process of claim 2, wherein the beta lactam is reacted with a methanesulfonic acid-amine salt of the substrate.
31. The process of claim 4, wherein the beta lactam is reacted with a methanesulfonic acid-amine salt of the substrate.
32. The process of claim 1, wherein the beta lactam is reacted with the triethylamine-acid salt of the substrate.
33. The process of claim 2, wherein the beta lactam is reacted with the triethylamine-acid salt of the substrate.
34. The process of claim 4, wherein the beta lactam is reacted with the triethylamine-acid salt of the substrate.
35. The process of claim 1, wherein the beta lactam is prepared by a process comprising:
(a) reacting a substrate of the formula

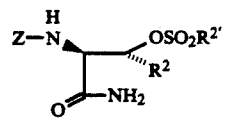

(wherein Z is benzyloxycarbonyl and R²' is alkyl, aryl, aralkyl, or alkylaryl) with a halosulfonic acid-pyridine complex in an organic solvent;
(b) reacting the so-reacted substrate with a base selected from alkali metal hydroxide, carbonate or bicarbonate in an aqueous solution to form the beta lactam wherein one of R² and R³ is hydrogen and R⁴ is SO₃⊖M⊕.

36. The process of claim 35, wherein the halosulfonic acid-pyridine complex is a complex of 2,6-lutidine and chlorosulfonic acid.
37. The process of claim 35, wherein the base is sodium hydroxide.

* * * * *